United States Patent [19]
Badorc et al.

[11] Patent Number: 5,719,143
[45] Date of Patent: Feb. 17, 1998

[54] POLYSUBSTITUTED 3-ACYLAMINO-5-PHENYL-1,4-BENZODIAZEPIN-2-ONE DERIVATIVES, PROCESS FOR THEIR PREPARATION AND THE PHARMACEUTICAL COMPOSITIONS CONTAINING THEM

[75] Inventors: Alain Badorc, Roquettes; Pierre Despeyroux, Portet-Garonne; Danièle Gully, Muret; Paul de Cointet; Daniel Fréhel, both of Toulouse; Jean-Pierre Maffrand, Portet/Garonne, all of France

[73] Assignee: Sanofi, Paris, France

[21] Appl. No.: 390,770

[22] Filed: Feb. 14, 1995

[30] Foreign Application Priority Data

Feb. 14, 1994 [FR] France ................... 94 01642
Jul. 12, 1994 [FR] France ................... 94 08665

[51] Int. Cl.$^6$ .................. C07D 243/24; A61K 31/395
[52] U.S. Cl. ............................ 514/221; 540/509
[58] Field of Search ..................... 514/221; 540/509

[56] References Cited

FOREIGN PATENT DOCUMENTS 0167919 6/1985 European Pat. Off. .
0376849 12/1989 European Pat. Off. .

OTHER PUBLICATIONS

Chemical Abstracts, vol. 72, No. 15, 13 Avril 1970, Columbus, Ohio, U.S.; abstract No. 79116k, p.414; *abrege* & JP-A-69026 871 (Tanabe Seiyaku Co. Ltd.).

Sato et al, Chemical Abstract 117: 69890 (1992).

Tokarshi et al, Chemical Abstracts, vol. 121 entry 221049 (1994).

Sato et al, Chemical Abstracts, vol. 113 entry 59237 (1990).

*Primary Examiner*—John M. Ford
*Attorney, Agent, or Firm*—Jacobson, Price, Holman & Stern, PLLC

[57] ABSTRACT

The invention relates to the compounds of formula (I)

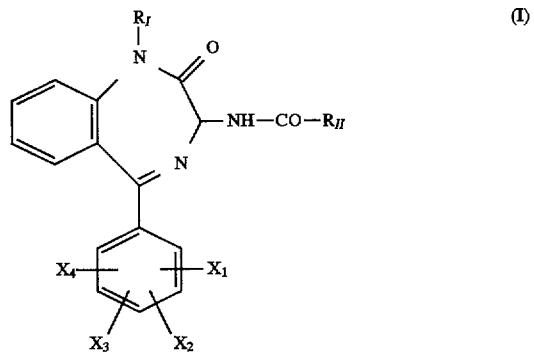

in which $R_I$, $R_{II}$, $X_1$, $X_2$, $X_3$ and $X_4$ are as defined in claim 1.

14 Claims, No Drawings

POLYSUBSTITUTED 3-ACYLAMINO-5-PHENYL-1,4-BENZODIAZEPIN-2-ONE DERIVATIVES, PROCESS FOR THEIR PREPARATION AND THE PHARMACEUTICAL COMPOSITIONS CONTAINING THEM

The present invention relates to 3-acylamino-5-phenyl-1,4-benzodiazepin-2-one derivatives and the salts thereof, to a process for their preparation and to the pharmaceutical compositions containing them.

The compositions of the present invention differ from other 1,4-benzodiazepine derivatives by their novel structure and by their new pharmacological properties. These compounds are 1,4-benzodiazepine derivatives in which the phenyl in position 5 of the benzodiazepine is at least trisubstituted.

This particular structure imparts unexpected and very advantageous pharmacological properties to the products according to the invention. Indeed, the compounds of the invention have an affinity for cholecystokinin receptors; more particularly, the subject of the present invention is new agonists for the cholecystokinin (CCK) receptors on the pancreatic amylase test.

CCK is a peptide widely distributed in the brain, especially in the cortex, the striatum, the hippocampus, the ventral tegmentum, the septum and the hypothalamus.

CCK is also secreted at the peripheral level by the small intestine, its action is manifested especially by the stimulation of vesicular contraction, an increase in bile secretion, the control of pancreatic enzyme secretion, an action on Gastric contractions and an action on intestinal motility. In some cases, it may act on arterial pressure and may influence immune systems.

In certain central neurones, CCK coexists with dopamine. It also plays a part in mechanisms involving acetylcholine, gaba, serotonin, opiates, somatostatin, substance P and ion channels.

Its administration brings about physiological modifications: palpebral ptosis, hypothermia, hyperglycaemia and catalepsy, and behavioural modifications: hypolocomotion, decrease in exploration, analgesia, action in learning, modification of sexual behaviour and satiety.

A CCK-receptor agonist, especially a CCKA-receptor agonist, may thus be used as a medicine in the treatment of certain disorders of feeding behaviour, of obesity, of diabetes, in disorders of emotional, sexual and mnemonic behaviour, in schizophrenia, in psychosis, in Parkinson's disease and in various disorders of the gastrointestinal area (Drugs of the Future, 1992, 17, No. 3, 197–206).

Hitherto, all of the 1,4-benzodiazepines described as having a good affinity for the CCKA receptors are antagonists.

Compounds which are ligands for the CCK receptors and for gastrin are known in the literature, an illustration thereof for example being Patent Application WO-93/20099.

There may also be mentioned, by way of example, Devazepide or L-365260, the respective formulae of which are

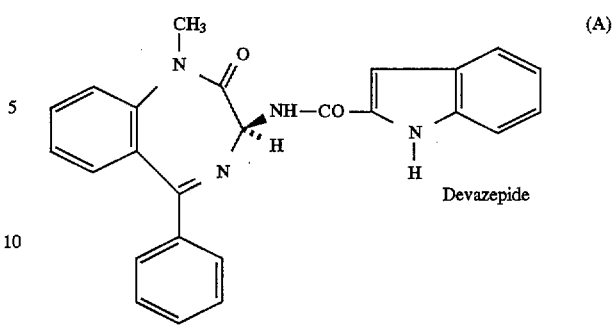
Devazepide (A)

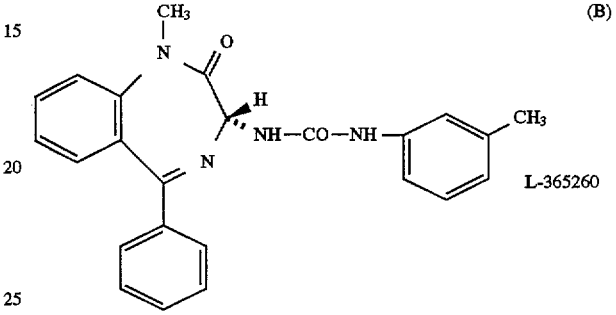
L-365260 (B)

CCK-receptor agonists of peptidic nature or having a structure very different from the compounds according to the present invention are described in the literature. For example, certain products having such properties are described in EP-A-0,383,690, WO 90/06937 and EP-A-0,376,849.

The compounds of the invention and the addition salts thereof with inorganic or organic acids correspond to the formula:

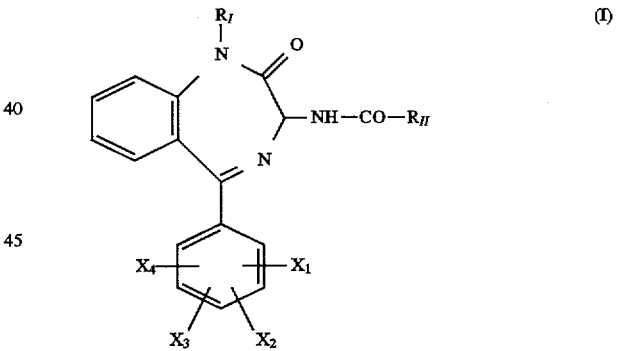
(I)

in which
$R_I$ represents
  (i) hydrogen;
  (ii) a $(C_1-C_4)$alkyl;
  (iii) a group —$CH_2$—CHOH—$(CH_2)_m$-Z in which
    m is 0 or 1 and Z represents a $(C_1-C_4)$alkyl group; $(C_3-C_8)$cycloalkyl group; aryl group optionally substituted with $(C_1-C_4)$alkyl, $(C_1-C_4)$alkoxy or halogen; or Z represents a saturated or unsaturated heterocycle which is optionally substituted with $(C_1-C_4)$alkyl, $(C_1-C_4)$alkoxy or halogen; or
  (iv) $R_I$ represents a group —$(CH_2)_n COR_o$ in which
    n represents 1 to 3,
    $R_o$ represents $OR_2$ or $NR_2R_3$, $R_2$ and $R_3$, which may or may not be identical, representing H or $(C_1-C_4)$ alkyl or alternatively $R_2$ and $R_3$ forming, together with the nitrogen atom to which they are attached, a saturated or unsaturated heterocycle;

$R_{II}$ represents
either (i) a nitrogen-containing aromatic heterocycle, $R_{IIa}$, chosen from quinoline, isoquinoline, benzimidazole and indole, the latter optionally being substituted on the nitrogen with a group W where W represents the group CO—($C_1$–$C_4$)alkyl; or the group $(CH_2)_nCOR_o$ in which n and $R_o$ are as defined for $R_I$, or (ii) a group

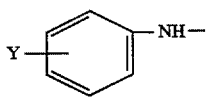  ($R_{IIb}$)

in which Y represents a halogen atom or a ($C_1$–$C_3$) alkyl or ($C_1$–$C_3$)alkoxy group;

$X_1$, $X_2$ and $X_3$ are identical or different and represent a ($C_1$–$C_3$)alkyl, a ($C_1$–$C_3$)alkoxy, a halogen atom or a trifluoromethyl group;

$X_4$ represents hydrogen or is identical to $X_1$, $X_2$ or $X_3$, and the stereoisomers thereof.

The term alkyl radical means linear or branched alkyl radicals of 1 to 4 carbon atoms.

The term saturated or unsaturated heterocycle means an aromatic or non-aromatic heterocycle chosen from furan, thiophene, pyrrole, imidazole, pyrrolidine, piperidine, piperazine, pyridine or morpholine.

A particular group of compounds according to the invention consists of the compounds of formula I in which $X_1$ is in position 2, $X_2$ is in position 4, $X_3$ is in position 6 and $X_4$ is either in position 3 or 5 of the phenyl radical.

Among these compounds, those are preferred in which at least three of the substituents $X_1$, $X_2$, $X_3$ or $X_4$ represent ($C_1$–$C_2$)alkyl or ($C_1$–$C_2$)alkoxy and in particular those chosen from methyl or methoxy groups in position 2, 4, 6 of the aromatic ring; moreover, $R_{IIa}$ preferably represents a substituted or unsubstituted indolyl.

Another group of preferred compounds consists of compounds in which two of the substituents $X_1$, $X_2$, $X_3$ and $X_4$ respectively represent a 2-($C_1$–$C_3$)alkoxy group and a 6-($C_1$–$C_3$)alkoxy group.

When $X_1$, $X_2$ or $X_3$ are a halogen atom, they are preferably the chlorine atom, but they may also represent a fluorine, bromine or iodine atom.

All of the compounds according to the invention possess an asymmetric centre and may thus exist in the form of optical isomers. The present invention equally comprises these isomers, either separately or as a mixture.

The addition salts with inorganic or organic acids may be, for example, the salts formed with hydrochloric acid, hydrobromic acid, nitric acid, sulphuric acid, phosphoric acid, acetic acid, formic acid, propionic acid, benzoic acid, maleic acid, fumaric acid, succinic acid, tartaric acid, citric acid, oxalic acid, glyoxylic acid, aspartic acid, alkanesulphonic acids such as methanesulphonic acid or ethanesulphonic acid, arylsulphonic acids, such as benzenesulphonic acid or paratoluenesulphonic acid, and arylcarboxylic acids.

Among the products of the invention which may be mentioned in particular are the derivatives corresponding to formula (I) above, and the addition salts thereof with inorganic or organic acids, characterized in that in the said formula (I), the substituent $R_{II}$ represents a group $R_{IIa}$ of formula

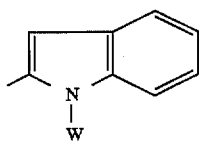

and in which W, $X_1$, $X_2$, $X_3$ and $X_4$ have the above meaning.

Among the preferred compounds of the invention, the following compounds may be mentioned:

N-[2,3-dihydro-5-(2,6-dimethoxy-4-methylphenyl)-1-methyl-2-oxo-1H-1,4-benzodiazepin-3-yl]-1H-2-indolecarboxamide;

[N-[2,3-dihydro-5-(2,6-dimethoxy-4-methylphenyl)-1-methyl-2-oxo-1H-1,4-benzodiazepin-3-yl]-2-aminocarbonyl-1H-indol-1-yl]acetic acid;

methyl {N-[2,3-dihydro-5-(2,6-dimethoxy-4-methylphenyl)-1-methyl-2-oxo-1H-1,4-benzodiazepin-3-yl]-2-aminocarbonylindol-1-yl}acetate;

dextrorotatory N-[2,3-dihydro-5-(2,6-dimethoxy-4-methylphenyl)-1-methyl-2-oxo-1H-1,4-benzodiazepin-3-yl]-1H-indole-2-carboxamide;

N-[2,3-dihydro-5-(2,3,6-trimethoxy-4-methylphenyl)-1-methyl-2-oxo-1H-1,4-benzodiazepin-3-yl]-1H-2-indolecarboxamide The compounds according to the invention may be prepared according to Scheme 1 below:

SCHEME 1

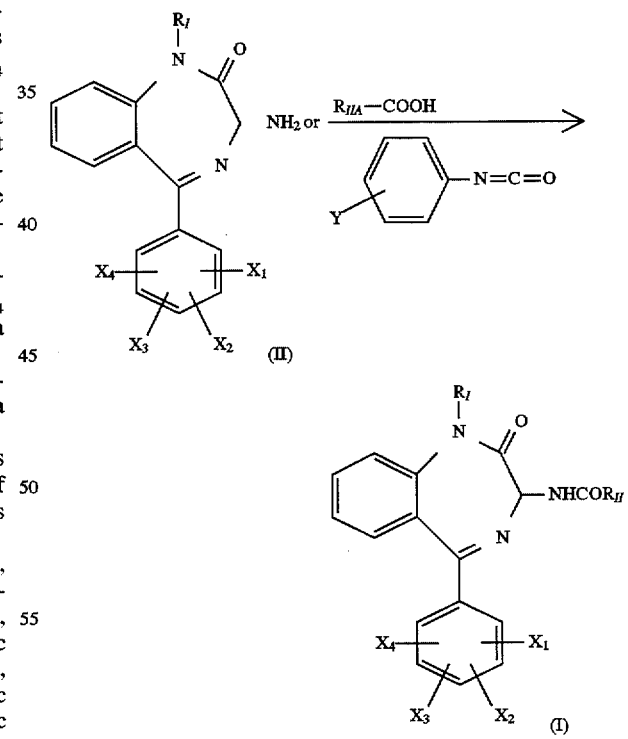

When $R_{II}$ represents a nitrogen-containing heterocycle $R_{IIa}$, the compounds of formula (I) may be prepared by coupling of a 3-amino-5-(substituted)phenyl-1-methyl-1,4-benzodiazepin-2-one of formula (II) under the usual conditions for acylation of an amine function with an acid of formula $R_{IIa}COOH$ in which the reactive groups of $R_{IIa}$ have optionally been protected, or with an activated form of the acid such as an acid halide, an acid anhydride or an activated ester obtained with the reactants commonly used in peptide synthesis.

When functions have been protected, the appropriate deprotection reaction is carried out, if necessary, after the coupling.

Some of the acids $R_{IIa}COOH$ are known and are even commercially available; the others are prepared using the methods known for similar molecules, especially according to the methods described in EP-A-432,040.

When $R_{II}$ represents a group $R_{IIb}$

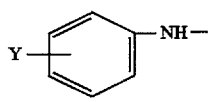
(R$_{IIb}$)

in which Y is as defined for (I), the corresponding ureas (I) may be prepared from the aminobenzodiazepine (II) with a substituted phenyl isocyanate of formula

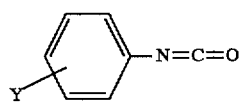

in which Y is as defined above. These isocyanate derivatives are commercially available or may be prepared by known methods.

The 3-amino-1,4-benzodiazepin-2-ones of formula (II) and the synthesis intermediates (V), (VI) and (VII) below are new and represent another aspect of the present invention.

According to another of its aspects, the present invention relates to a process for the preparation of the compounds of formula (I), characterized in that a substituted benzene derivative of formula

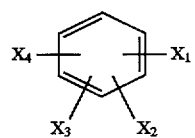
(III)

in which $X_1$, $X_2$, $X_3$ and $X_4$ are as defined for (I), is reacted with an isatoic anhydride of formula

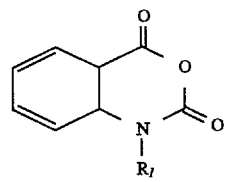
(IV)

in which $R_I$ is as defined for (I), to give the diphenyl ketone of formula

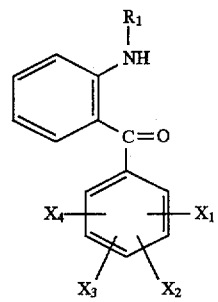
(V)

in which $X_1$, $X_2$, $X_3$, $X_4$ and $R_I$ are as defined for (I), which compound is then reacted with a halo ketone of formula Hal-CH$_2$COCl in which Hal preferably represents a bromine or chlorine atom, which compound is then cyclized, for example in the presence of ammonia, to give the benzodiazepine of formula:

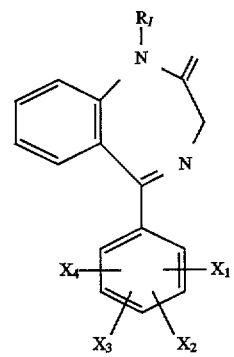
(VI)

in which $X_1$, $X_2$, $X_3$, $X_4$ and $R_I$ are as defined for (I), it being understood that if $R_I$ is a (C$_2$-C$_4$)alkyl, the compound (VI) may also be prepared by alkylation of the amide (VI with $R_I$=H), by the action of a derivative AlkI in which Alk represents a C$_2$-C$_4$ alkyl, after which the oxime of compound (VI) is prepared by reacting potassium tert-butoxide and isoamyl nitrite, (CH$_3$)$_2$CH—CH$_2$—CH$_2$—ONO, to give the benzodiazepine of formula

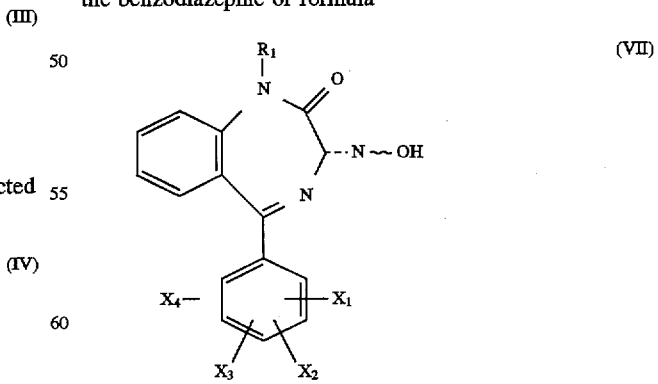
(VII)

in which $R_I$, $X_1$, $X_2$, $X_3$ and $X_4$ are as defined for (I), in order subsequently to reduce the oxime function by hydrogen in the presence of a catalyst such as ruthenium on charcoal, to give the aminobenzodiazepin-2-one of formula

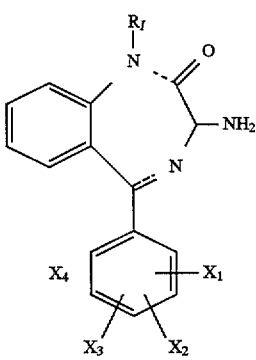

(II)

in which $X_1$, $X_2$, $X_3$, $X_4$ and $R_I$ are as defined for (I), in order to subject it to the action either of an acid of formula

$R_{IIa}COOH$ or one of the activated forms thereof in which $R_{IIa}$ is as defined for (I)

or of a phenyl isocyanate of formula

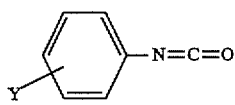

in which Y is as defined for (I), to give the compounds (I) according to the invention or one of the salts thereof.

The intermediates of formula (II), (V), (VI) and (VII) are new compounds which form part of the invention. The stereoisomers and addition salts of the compounds of formula II are also part of the invention.

The 3-aminobenzodiazepin-2-ones (II) are prepared according to methods that are known and described in the literature, for example according to Patent Application WO/9307130 by reduction of the oxime (VII) by catalytic hydrogenation or reduction using a suitable metal under acidic conditions. Suitable hydrogenation catalysts include, for example, catalysts of noble metals such as ruthenium or rhodium which may be bound to charcoal, for example. This reaction is preferably performed in a suitable organic solvent such as an alcohol, for example methanol, at temperatures of 60°–70° C., preferably at 60° C. Suitable reduction methods using metals include the use of zinc and trifluoroacetic acid in a suitable solvent such as acetic acid, at approximately 40°–50° C.

The oximes (VII) are prepared by reaction of isoamyl nitrite in the presence of a base such as alkali metal alkoxides, for example potassium tert-butoxide, according to M. G. Bock et al., J. Org. Chem. 1987, 52, 3232–3239 for example.

The benzodiazepines (VI) are obtained according to M. G. Bock et al., J. Org. Chem. 1987, 52, 3232–3239 by cyclization between a halo ketone $Hal-CH_2-COCl$ and a diphenyl ketone of formula (V) which is also prepared according to Bock et al. The diphenyl ketone (V) is obtained by coupling of an isatoic anhydride of formula (IV) in which $R_I$ represents hydrogen or a methyl.

When $R_I$ is a $C_2$-$C_4$ alkyl, the benzodiazepines of formula (VI) are prepared by alkylation of (VI, with R=H) in the presence of an alkali metal hydride such as sodium hydride, in an organic solvent such as dimethylformamide, in the presence of an alkylating agent AlkX in which Alk represents a $C_2$-$C_4$ alkyl and X represents a halogen, preferably iodine, according to EP-167,919.

The 3-aminobenzodiazepin-2-ones (II) may also be prepared by application or adaptation of the methods described in Patents WO 93/07130, EP-167,919, EP-540,039 or according to B. E. Evans, J. Med. Chem., 1988, 31, 2235.

Another alternative to the preparation of the 3-aminobenzodiazepin-2-ones, in particular for those in which the phenyl in position 5 is tetrasubstituted, consists of an adaptation, to these compounds, of the method described by M. G. Bock et al., J. Org. Chem., 1987, 52, 3232. The preparation of the diphenyl ketone may be adapted according to J. R. Lewis et al., Tetrahedron, 1981, 37, 209 by reaction of 2-methyl-1,3-benzoxazin-4-one with aryllithium reagents.

The preparation of the optically pure compounds of formula (I) was carried out by using and adapting the process used by M. G. Bock et al., J. Org. Chem., 1987, 52, 3232–3239 and according to the preparations below according to Scheme 2 which follows:

SCHEME 2

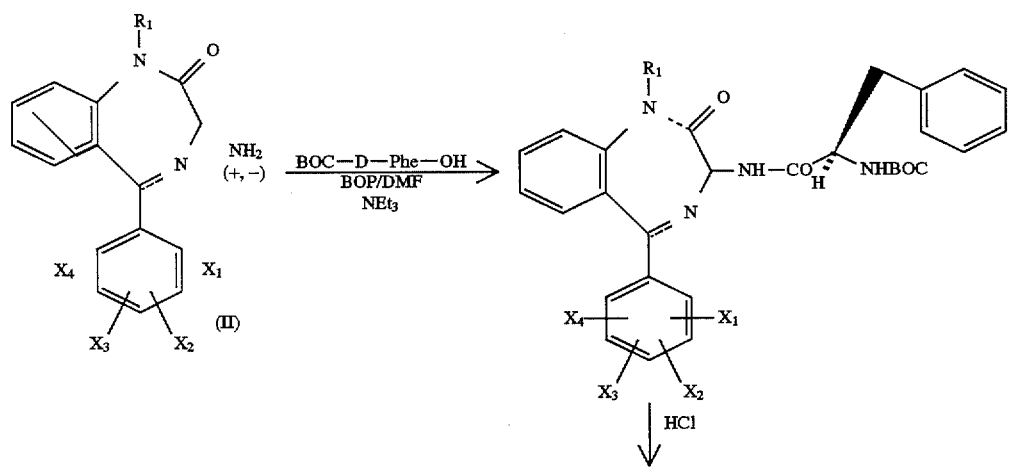

-continued
SCHEME 2

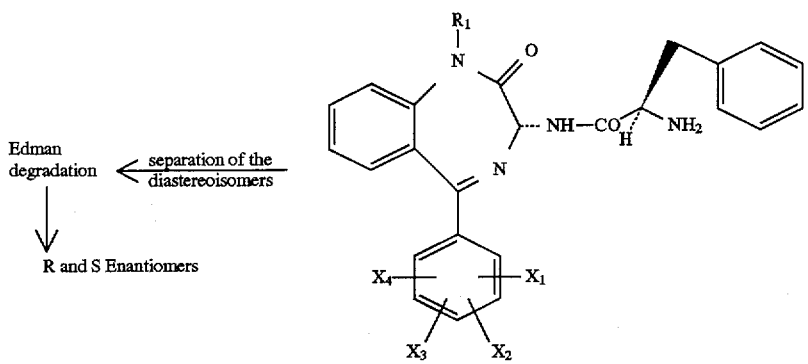

Edman degradation ← separation of the diastereoisomers

↓

R and S Enantiomers

According to another of its aspects, the subject of the invention is also medicines comprising the compounds (I) below.

These compounds have formed the subject of in vitro affinity measurement studies concerning the CCKA receptors.

This affinity is between 0.5 and 100 nM with a selectivity for the CCKA receptors over the CCKB receptors which may reach a factor of 10,000 for the compound of Example 1, for example.

Other compounds of the invention (compounds of Examples 6 and 7) have an affinity for the CCKB receptor which is identical to or greater than that obtained for the CCKA receptor.

A study of the agonist effect towards the CCKA receptors was demonstrated by measuring as follows the amylase secretion produced. Pancreatic acinar cells are obtained by enzymatic digestion (collagenase) of the pancreas of a rat which has been fasted for 18 hours. Aliquots (485 µl) are incubated at 37° C. for 30 minutes in the presence of increasing concentrations of agonist according to Jensen et al., J. Biol., Chem., 1982, 257, (10), 5554. The incubation is stopped by a 15-second centrifugation. The supernatant is kept in an ice-bath in order to measure the amylase content according to the technique of Ceska et al., Clin., Chim., Acta, 1969, 26, 437 (phadbas reagent). The compounds to be tested are dissolved in dimethyl sulphoxide and then in incubation buffer.

The compounds according to the invention behave as CCK-receptor agonists with $EC_{50}$s (concentration of product which induces 50% of the maximum response obtained with CCK itself) of the order of one nanomole.

The agonist effect demonstrated in this in vitro model was confirmed in an in vivo biliary emptying model in fasted mice according to a procedure described by D. Gully et al., European J. Pharmacol., 1993, 232, 13–19. The compounds are administered orally one hour before the sacrifice. The bile vesicle is removed and then weighed and the results, expressed in mg/kg of body weight, reveal for the compound of Example 10, for example, an $ED_{50}$ of 0.3 mg/kg.

Consequently, the compounds of formula (I) are used, as CCK-receptor agonists, for the preparation of medicines intended for the treatment of certain disorders of eating behaviour, of obesity, of diabetes, in disorders of emotional, sexual and mnemonic behaviour, in psychosis and especially schizophrenia, in Parkinson's disease and in various disorders in the gastrointestinal area.

The compounds of formula (I) are of little toxicity; their toxicity is compatible with their use as medicines for treating the above disorders and diseases.

The compounds of formula (I) may be formulated in pharmaceutical compositions for administration to mammals, including man, for the treatment of the above-mentioned diseases.

The dosage, which varies depending on the treatment and depending on the complaint in question, may range, for example, between 0.05 and 100 mg per day orally in adults. A subject of the present invention is also the pharmaceutical compositions which contain one of the above compounds as active principle. These compositions are produced so that they can be administered via the digestive or parenteral route.

In the pharmaceutical compositions of the present invention for oral, sublingual, subcutaneous, intramuscular, intravenous, transdermal, local or rectal administration, the active ingredient may be administered in unit administration forms, as a mixture with conventional pharmaceutical supports, to animals and to humans. The appropriate unit administration forms comprise oral forms such as tablets, gelatin capsules, powders, granules and oral solutions or suspensions, sublingual and buccal administration forms, subcutaneous, intramuscular, intravenous, intranasal or intraocular administration forms and rectal administration forms.

When a solid composition in the form of tablets is prepared, the main active ingredient is mixed with a pharmaceutical vehicle such as gelatin, starch, lactose, magnesium stearate, talc, gum arabic or the like. The tablets may be coated with sucrose or other suitable materials or alternatively they may be treated such that they have a prolonged or delayed activity and such that they release a predetermined amount of active principle continuously.

A preparation in gelatin capsules is obtained by mixing the active ingredient with a diluent and by pouring the mixture obtained into soft or hard gelatin capsules.

A preparation in the form of a syrup or an elixir may contain the active ingredient in combination with a sweetener, preferably a non-calorific sweetener, methylparaben and propylparaben as antiseptic agent, as well as a flavouring agent and a suitable dye.

The water-dispersible powders or granules may contain the active ingredient as a mixture with dispersing agents or wetting agents, or suspension agents, such as polyvinylpyrrolidone, as well as with sweeteners or flavour adjusters.

For rectal administration, use is made of suppositories which are prepared with binders which melt at the rectal temperature, for example cocoa butter or polyethylene glycols.

For parenteral, intranasal or intraocular administration, aqueous suspensions, isotonic saline solutions or sterile and injectable solutions which contain pharmacologically compatible dispersing agents and/or wetting agents, for example propylene glycol or butylene glycol, are used.

The active principle may also be formulated in the form of microcapsules, optionally with one or more supports or additives.

The composition may be in the form of a unit dose comprising from 0.05 to 100 mg of active principle.

In the following text, examples of implementation of the invention are described, as well as processes for the preparation of certain synthesis intermediates. The melting points, m.p., indicated were determined in a capillary and are expressed in degrees Celsius.

The examples which follow, given without any limitation being implied, illustrate the invention.

PREPARATION 1

(2,6-Dimethoxy-4-methylphenyl)(2-methylaminophenyl) Ketone (Compound 1)

To a solution of 30 g of 3,5-dimethoxytoluene in 400 ml of tetrahydrofuran are added, at a temperature in the region of −20° C., 129 ml of 1.6M butyllithium in hexane. Once the introduction is complete, the reaction mixture is brought to a temperature of 0° C. and is then stirred for 1 hour. It is cooled to −20° C. and 36.67 g of N-methylisatoic anhydride are added portionwise. The mixture is allowed to return to room temperature and is stirred over 2 hours, followed by addition of 500 ml of water and extraction with ethyl acetate. The organic phase is washed with water, dried over sodium sulphate and evaporated under vacuum. The residue is purified by chromatography on silica gel, eluent: toluene/ethyl acetate 9/1. The fractions of pure product are concentrated under vacuum and the residue is crystallized from isopropyl ether, filtered and dried. Beige crystals melting at 215° C. are obtained; Yield=78%.

The following compounds may also be prepared in the same way:

(2,4,6-Trimethoxyphenyl)(2-methylaminophenyl) ketone; m.p.=190° C.; Yield=86% (Compound 2).
(2,3,6-Trimethoxy-4-methylphenyl)(2-methylaminophenyl) ketone; m.p.=141° C.; Yield=81% (Compound 3).

PREPARATION II

N-[2-(2,6-Dimethoxy-4-methylbenzoyl)phenyl]-N-methylbromoacetamide (Compound 4)

To a mixture of 10 g of (2,6-dimethoxy-4-methylphenyl) (2-methylaminophenyl) ketone in 100 ml of dichloromethane and 20 ml of water, cooled to −10° C., are added dropwise 6.34 g of bromoacetyl chloride in 20 ml of dichloromethane. The reaction mixture is allowed to return to room temperature and is then stirred vigorously for 2 hours. The phases are separated after settling has taken place and the organic phase is successively washed with water, dried over sodium sulphate and evaporated to dryness to give beige crystals melting at 121° C.; Yield=99%.

The following compounds can also be prepared in the same way:

N-[2-(2,4,6-Trimethoxybenzoyl)phenyl]-N-methylbromoacetamide; m.p.=118° C.; Yield=92% (Compound 5).
N-[2-(2,3,6-Trimethoxy-4-methylbenzoyl)phenyl]-N-methylbromoacetamide; oil, Yield=100% (Compound 6).

PREPARATION III 1,3-Dihydro-5-(2,6-dimethoxy-4-methylphenyl)-1-methyl-1,4-benzodiazepin-2-one (Compound 7)

14 g of N-[2-(2,6-dimethoxy-4-methylbenzoyl)phenyl]-N-methylbromoacetamide are dissolved in 300 ml of methanol cooled to −10° C. and ammonia is bubbled through for 2 hours. The reaction mixture is then heated at reflux for 3 hours, followed by evaporation to dryness. The residue is then taken up in dichloromethane and then the organic phase is successively washed with water, dried over sodium sulphate and evaporated to dryness. The residue is purified by chromatography on a column of silica gel, eluent: dichloromethane/methanol 95/5.

Concentration of the fractions of pure product gives white crystals melting at 200° C.; Yield=89%.

The following are prepared in the same way:

1,3-Dihydro-5-(2,4,6-trimethoxyphenyl)-1-methyl-1,4-benzodiazepin-2-one, m.p.=161° C.; Yield=89% (Compound 8), and
1,3-Dihydro-5-(2,3,6-trimethoxy-4-methylphenyl)-1-methyl-1,4-benzodiazepin-2-one, m.p.=180° C., Yield=4% (Compound 9).

PREPARATION IV 1,3-Dihydro-5-(2,6-dimethoxy-4-methylphenyl)-3-hydroxyimino-1-methyl-1,4-benzodiazepin-2-one (Compound 10)

To a suspension of 9 g of 1,3-dihydro-5-(2,6-dimethoxy-4-methylphenyl)-1-methyl-1,4-benzodiazepin-2-one in 300 ml of toluene are added portionwise, with cooling to −20° C., 7.8 g of potassium tert-butoxide, then the temperature is allowed to rise slowly to 0° C. over 35 minutes, the mixture is cooled to −20° C. and 3.9 g of isoamyl nitrite in 50 ml of toluene are added dropwise. The reaction mixture is then stirred at 0° C. for 90 minutes, followed successively by pouring of the reaction mixture into water, adjustment of the pH to 4 with acetic acid, extraction with ethyl acetate, washing of the organic phase with water, drying over sodium sulphate and evaporation to dryness. The residue is crystallized from isopropyl ether, filtered and dried to give beige crystals melting at 150° C.; Yield=76%.

The following are prepared in the same way:

1,3-Dihydro-5-(2,4,6-trimethoxyphenyl)-1-methyl- 1,4-benzodiazepin-2-one, m.p.=155° C.; Yield=80% (Compound 11)
1,3-Dihydro-5-(2,3,6-trimethoxy-4-methylphenyl)-1-methyl-1,4-benzodiazepin-2-one, m.p.=144° C.; Yield=83% (Compound 12).

PREPARATION V

3-Amino-1,3-dihydro-5-(2,6-dimethoxy-4-methylphenyl)-1-methyl-1,4-benzodiazepin-2-one (Compound 13)

6.4 g of 1,3-dihydro-5-(2,6-dimethoxy-4-methylphenyl)-3-hydroxyimino-1-methyl-1,4-benzodiazepin-2-one are placed in 180 ml of methanol with 1.32 g of 5% ruthenium/C in an autoclave, which is heated to 60° C. and hydrogenated under a hydrogen pressure of 6 bar for 22 hours, followed successively by cooling of the reaction mixture, filtration of the catalyst and evaporation to dryness. The residue is taken up in acetone and the product is purified by salification via its oxalate intermediate. Beige crystals of the oxalate of the expected product are obtained, melting at 170° C.; Yield=80%.

The following are prepared in the same way:

3-Amino-1,3-dihydro-5-(2,4,6-trimethoxyphenyl)-1-methyl-1,4-benzodiazepin-2-one oxalate, m.p.=155° C.; Yield=83% (Compound 14), and
3-amino-1,3-dihydro-5-(2,3,6-trimethoxy-4-methylphenyl)-1-methyl-1,4-benzodiazepin-2-one, which is obtained in the form of an oil; Yield=75% (Compound 15).

SEPARATION OF THE DIASTEREOISOMERS OF THE COMPOUNDS OF FORMULA (II)

PREPARATION VI

Step 1

1.73 g of 3-amino-1,3-dihydro-5-(2,6-dimethoxy-4-methylphenyl)-1-methyl-1,4-benzodiazepin-2-one are dissolved in 30 ml of dimethylformamide in the presence of 1.42 g of BOC-D-phenylalanine, followed by cooling to 5° C. and addition of 1.07 ml of triethylamine and then 2.4 g of BOP. The reaction mixture is allowed to return to room temperature and is left stirring overnight. It is then poured into water and extracted with ethyl acetate. The organic phase is washed with water, separated out after settling of the phases, dried over $Na_2SO_4$, filtered and concentrated under vacuum. An oily residue of 2-tert-butoxycarbonylamino-N-[2,3-dihydro-5-(2,6-dimethoxy-4-methylphenyl)-1-methyl-2-oxo-1H-1,4-benzodiazepin-3-yl]-3-phenylpropionamide, obtained in quantitative yield, is used as it is for the following step (Compound 16).

Step 2

4.6 g of 2-tert-butoxycarbonylamino-N-[2,3-dihydro-5-(2,6-dimethoxy-4-methylphenyl)-1-methyl-2-oxo-1H-1,4-benzodiazepin-3-yl]-3-phenylpropionamide, obtained above are dissolved in 30 ml of ethyl acetate, the mixture is cooled to 0° C. and 30 ml of 5N solution of hydrogen chloride in ethyl acetate are then added dropwise.

Once the introduction is complete, the solution is allowed to return to room temperature and is stirred for 3 hours. The reaction mixture is poured into ethyl ether and the precipitate formed is isolated by filtration and is then successively washed with ethyl ether and dried to give 2-amino-N-[2,3-dihydro-5-(2,6-dimethoxy-4-methylphenyl)-1-methyl-2-oxo-1H-1,4-benzodiazepin-3-yl]-3-phenylpropionamide in the form of white crystals in a yield of 90%; m.p.=165° C. (Compound 17).

Step 3

The diastereoisomers obtained in the above step are separated by preparative HPLC. Separation of the diastereoisomers is performed on a PROCHROM LC50 apparatus with axial dynamic compression. The stationary phase used is a KROMASIL reverse phase of porosity 100 Å. The elution takes place in isocratic mode with 65% of (water +1% trifluoroacetic acid) and 35% of (acetonitrile/water 90/10 with 0.8‰ of trifluoroacetic acid) at a flow rate of 120 ml/minute and UV detection at 220 nm. With 3.7 g of racemic mixture from the above step, and after freeze-drying and basification, each of the two stereoisomers is obtained in the form of a foam, in a separation yield of 45%.

PREPARATION VII

Synthesis of the Dextrorotatory and Laevorotatory Enantiomers of 3-Amino-1,3-dihydro-5-(2,6-dimethoxy-4-methylphenyl)-1-methyl-1,4-benzodiazepin-2-one The two enantiomers are obtained in two steps from the two diasteroisomers isolated above, using the conventional Edman degradation method according to P. Edman, Acta Chem; Scand., 1950, 4, 283.

Synthesis of the Dextrorotatory Enantiomer

Step 1 (Compound 18)

720 mg of a diastereoisomer obtained in Step 3 of Preparation VI above are dissolved in 10 ml of dichloromethane and 220 mg of phenyl isothiocyanate are added. The mixture is heated at reflux for 1 hour, followed by evaporation of the reaction mixture under vacuum and crystallization of the residue in isopropyl ether. Crystals melting at 140° C. are obtained; Yield=95%.

Step 2

860 mg of the thiourea derivative obtained in the above step are dissolved in 20 ml of ethyl acetate, cooled to a temperature in the region of 5° C., and 10 ml of 5N solution of hydrogen chloride in ethyl acetate are added dropwise. to room temperature and is stirred for 2 hours, followed by evaporation and chromatography on a column of silica gel (eluent: dichloromethane/methanol/water/acetic acid 90/10/1/1). The fractions of pure product are evaporated under vacuum, followed successively by evaporation, basification of the residue, extraction with dichloromethane, washing with water and drying. After evaporation, crystals melting at 139° C. are obtained; Yield=89%. $[\alpha]_D^{20}=+140$ (c=0.2 in $CH_3OH$).

Synthesis of the Laevorotatory Enantiomer
(Compound 19)

The laevorotatory enantiomer is obtained in a similar manner, by using the Edman degradation on the other diastereoisomer. Crystals melting at 139° C. are obtained; Yield=85%; $[\alpha]_D^{20}=-146$ (c=0.2 in $CH_3OH$).

EXAMPLE 1

(1): $R_I = CH_3$; $R_{II} =$ 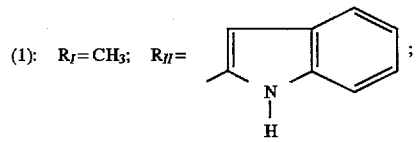 ;

$X_1 = 2\text{-}OCH_3$; $X_2 = 6\text{-}OCH_3$; $X_3 = 4\text{-}CH_3$; $X_4 = H$ 0.47 ml of pyridine is dissolved in 10 ml of dichloromethane, cooled to −5° C., and 0.68 ml of thionyl chloride is added dropwise, the mixture is stirred for 20 minutes at the same temperature and then 208 mg of indole-2-carboxylic acid are added portionwise with stirring for 30 minutes. 400 mg of 3-amino-1,3-dihydro-5-(2,6-dimethoxy-4-methylphenyl)-1-methyl-1,4-benzodiazepin-2-one are added portionwise and the reaction mixture is then allowed to return to room temperature and is stirred for 16 hours. Water is added to the reaction mixture and the precipitate formed is filtered off and dried to give white crystals of N-[2,3-dihydro-5-(2,6-dimethoxy-4-methylphenyl)-1-methyl-2-oxo-1H-1,4-benzodiazepin-3-yl]-1H-2-indolecarboxamide melting with decomposition at 310° C.; Yield=79%.

EXAMPLE 2

(1): $R_I$=CH$_3$; $R_{II}$= 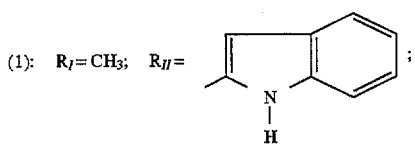

$X_1$ = 2-OCH$_3$;  $X_2$ = 6-OCH$_3$;  $X_3$ = 4-OCH$_3$;  $X_4$ = H

By performing the process according to Example 1 and using 3-amino-1,3-dihydro-5-(2,4,6-trimethoxyphenyl)-1-methyl-1,4-benzodiazepin-2-one, N-[2,3-dihydro-5-(2,4,6-trimethoxyphenyl)-1-methyl-1-oxo-1H-1,4-benzodiazepin-3-yl]-1H-2-indolecarboxamide is obtained; m.p.=297° C.; Yield=87%.

EXAMPLE 3

(1): $R_I$=CH$_3$; $R_{II}$= 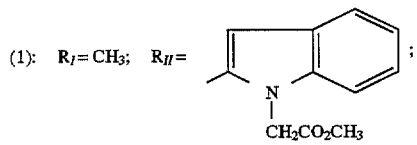

$X_1$ = 2-OCH$_3$;  $X_2$ = 6-OCH$_3$;  $X_3$ = 4-CH$_3$;  $X_4$ = H

To a solution of 0.37 g of 3-amino-1,3-dihydro-5-(2,6-dimethoxy-4-methylphenyl)-1-methyl-1,4-benzodiazepin-2-one in 10 ml of dimethylformamide, cooled to 5° C., are added 0.28 g of 1-methoxycarbonylmethyl-1H-indole-2-carboxylic acid, 578 mg of BOP and 0.303 ml of triethylamine. The reaction mixture is stirred overnight at room temperature and is then poured into water and extracted with ethyl acetate. The organic phase is successively washed with water, dried over sodium sulphate and evaporated to dryness. The crystals obtained are recrystallized from a mixture of isopropyl ether and isopropanol. White crystals of methyl {N-[2,3-dihydro-5-(2,6-dimethoxy-4-methylphenyl)-1-methyl-2-oxo-1H-1,4-benzodiazepin-3-yl]-2-aminocarbonylindol-1-yl}acetate are obtained, melting at 242° C.; Yield=77%.

EXAMPLE 4

(1): $R_I$=CH$_3$; $R_{II}$= 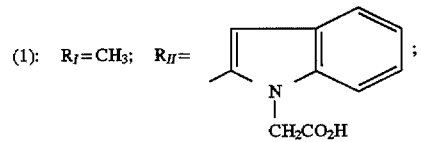

$X_1$ = 2-OCH$_3$;  $X_2$ = 6-OCH$_3$;  $X_3$ = 4-CH$_3$;  $X_4$ = H 220 mg of methyl N-[2,3-dihydro-5-(2,6-dimethoxy-4-methylphenyl)-1-methyl-2-oxo-1H-1,4-benzodiazepin-3-yl-2-aminocarbonyl-1H-indol-1-yl]acetate are dissolved in 10 ml of methanol and 1 ml of 1N sodium hydroxide is added dropwise, followed by stirring overnight at room temperature. The mixture is taken up in water and extracted with ethyl ether. The aqueous phase is acidified to pH 3 with potassium hydrogen sulphate and is extracted with dichloromethane, dried over sodium sulphate and evaporated to dryness. The {N-[2,3-dihydro-5-(2,6-dimethoxy-4-methylphenyl)-1-methyl-2-oxo-1H-1,4-benzodiazepin-3-yl]-2-aminocarbonyl-1H-indol-1-yl}acetic acid obtained is crystallized from isopropyl ether to give white crystals melting at 138° C.; Yield=75%.

EXAMPLE 5

(1): $R_I$=CH$_3$; $R_{II}$= 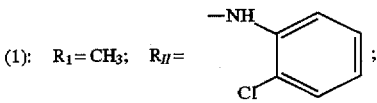

$X_1$ = 2-OCH$_3$;  $X_2$ = 6-OCH$_3$;  $X_3$ = 4-CH$_3$;  $X_4$ = H

To 56 mg of 3-amino-1,3-dihydro-5-(2,6-dimethoxy-4-methylphenyl)-1-methyl-1,4-benzodiazepin-2-one in 10 ml of dichloromethane is added 0.022 ml of 2-chlorophenyl isocyanate and the reaction mixture is then stirred at room temperature overnight. It is concentrated under vacuum and the residue is crystallized from isopropyl ether to give 3-(2-chlorophenylureido)-1,3-dihydro-5-(2,6-dimethoxy-4-methylphenyl)-1-methyl-1,4-benzodiazepin-2-one; m.p.=260° C.; Yield=91%.

EXAMPLE 6

(1): $R_I$=CH$_3$; $R_{II}$=H— 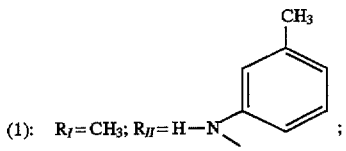

$X_1$ = 2-OCH$_3$;  $X_2$ = 6-OCH$_3$;  $X_3$ = 4-CH$_3$;  $X_4$ = H

By using 3-amino-1,3-dihydro-5-(2,6-dimethoxy-4-methylphenyl)-1-methyl-1,4-benzodiazepin-2-one as above and by condensing it as above with 3-methylphenyl isocyanate, 1,3-dihydro-5-(2,6-dimethoxy-4-methylphenyl)-1-methyl-3-(3-methylphenylureido)-1,4-benzodiazepin-2-one is obtained; m.p.=260° C.; Yield=94%.

EXAMPLE 7

(1): $R_I$=CH$_3$; $R_{II}$= 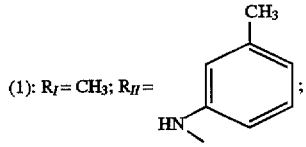

$X_1$ = 2-OCH$_3$;
$X_2$ = 4-OCH$_3$;
$X_3$ = 6-OCH$_3$;
$X_4$ = H

By condensing 3-amino-1,3-dihydro-1-methyl-5-(2,4,6-trimethoxyphenyl)-1,4-benzodiazepin-2-one with 3-methylphenyl isocyanate, 1,3-dihydro-1-methyl-3-(3-methylphenylureido)-5-(2,4,6-trimethoxyphenyl)-1,4-benzodiazepin-2-one is obtained; m.p.=240° C., Yield=94%.

EXAMPLE 8

(1): $R_I$=CH$_3$; $R_{II}$= 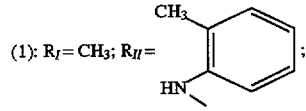

$X_1$ = 2-OCH$_3$;
$X_2$ = 4-OCH$_3$;
$X_3$ = 6-OCH$_3$;
$X_4$ = H

By performing the process according to Example 7 and using 2-methylphenyl isocyanate, 1,3-dihydro-1-methyl-3-(2-methylphenylureido)-5-(2,4,6-trimethoxyphenyl)-1,4-benzodiazepin-2-one is obtained; m.p.=50° C.; Yield=92%.

EXAMPLE 9

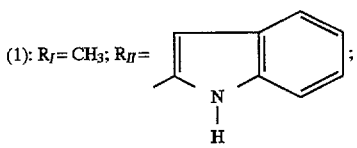

(1): $R_I = CH_3$; $R_{II} =$ $X_1 = 2\text{-OCH}_3$;
$X_2 = 4\text{-CH}_3$;
$X_3 = 6\text{-OCH}_3$;
$X_4 = H$ laevorotatory enantiomer To a solution of 0.38 g of the laevorotatory enantiomer of 3-amino-1,3-dihydro-5-(2,6-dimethoxy-4-methylphenyl)-1-methyl-1,4-benzodiazepin-2-one in 10 ml of dimethylformamide, cooled to 5° C., are added 0.52 g of BOP and 0.19 g of indole-2-carboxylic acid, followed by 0.23 ml of triethylamine. The reaction mixture is stirred overnight at room temperature and is then poured into water and extracted with ethyl acetate, dried over sodium sulphate and evaporated to dryness. The product is purified by chromatography on a column of silica gel (eluent: dichlormethane/methanol: 95/5). The fractions of pure product are evaporated to dryness and the residue is crystallized from isopropyl ether. White crystals of (−)-N-[2,3-dihydro-5-(2,6-dimethoxy-4-methylphenyl)-1-methyl-2-oxo-1H-1,4-benzodiazepin-3-yl]-1H-indol-2-carboxamide are obtained, melting at 135° C.; Yield=81%; $[\alpha]_D^{20}=-408$ (c=0.35 in 1N HCl/CH$_3$OH—50/50).

EXAMPLE 10

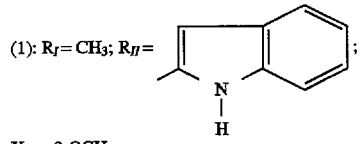

(1): $R_I = CH_3$; $R_{II} =$ $X_1 = 2\text{-OCH}_3$;
$X_2 = 4\text{-CH}_3$;
$X_3 = 6\text{-OCH}_3$;
$X_4 = H$ dextrorotatory enantiomer This compound is obtained in an identical manner to that of the other enantiomer (Example 9), starting with the dextrorotatory enantiomer of 3-amino-1,3-dihydro-5-(2,6-dimethoxy-4-methylphenyl)-1-methyl-1,4-benzodiazepin-2-one. White crystals of dextrorotatory (+)-N-[2,3-dihydro-5-(2,6-dimethoxy-4-methylphenyl)-1-methyl-2-oxo-1H-1,4-benzodiazepin-3-yl]-1H-indole-2-carboxamide are obtained, melting at 135° C.; Yield=78%; $[\alpha]_D^{20}=+412$ (c=0.32 in 1N HCl/CH$_3$OH—50/50).

EXAMPLE 11

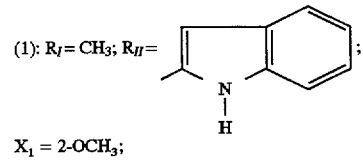

(1): $R_I = CH_3$; $R_{II} =$ $X_1 = 2\text{-OCH}_3$;
$X_2 = 3\text{-OCH}_3$;
$X_3 = 6\text{-OCH}_3$;
$X_4 = 4\text{-CH}_3$ By performing the process according to Example 3, starting with 3-amino-1,3-dihydro-5-(2,3,6-trimethoxy-4-methylphenyl)-1-methyl-1,4-benzodiazepin-2-one and indole-2-carboxylic acid, crystals of N-[2,3-dihydro-5-(2,3,6-trimethoxy-4-methylphenyl)-1-methyl-2-oxo-1H-1,4-benzodiazepin-3-yl]-1H-indole-2-carboxamide are obtained, melting at 290° C.; Yield=68%.

We claim:

1. A compound of formula (I):

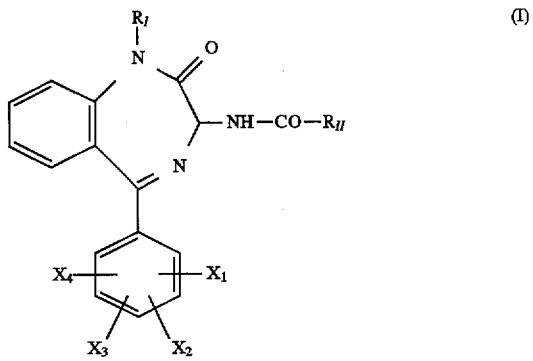

in which $R_I$ is selected from (i) hydrogen; (ii) a (C$_1$–C$_4$) alkyl; (iii) a group —CH$_2$—CHOH—(CH$_2$)$_m$-Z in which m is selected from 0 and 1 and Z is selected from a (C$_1$–C$_4$) alkyl group; (C$_3$–C$_8$) cycloalkyl group; (C$_6$–C$_{10}$) carbocyclic aryl group optionally substituted with (C$_1$–C$_4$) alkyl, (C$_1$–C$_4$) alkoxy and halogen; saturated or unsaturated heterocycle selected from the group consisting of furan, thiophene, pyrrole, imidazole, pyrrolidine, piperidine, piperazine, pyridine, and morpholine, optionally substituted with a radical selected from (C$_1$—C$_4$) alkyl, (C$_1$—C$_4$) alkoxy and halogen; and (iv) a group —(CH$_2$)$_n$COR$_0$ in which n is selected form 1 to 3, R$_0$ is selected from OR$_2$ and NR$_2$R$_3$, R$_2$ and R$_3$, which may or may not be identical, being selected from H and (C$_1$–C$_4$) alkyl or alternatively R$_2$ and R$_3$ forming, together with the nitrogen atom to which they are attached, a saturated or unsaturated heterocycle selected from the group consisting of furan, thiophene, pyrrole, imidazole, pyrrolidine, piperidine, piperazine, pyridine, and morpholine;

R$_{II}$ is selected from (i) a nitrogen-containing aromatic heterocycle, R$_{IIa}$, chosen from quinoline, isoquinoline, benzimidazole, indole and indole substituted on the nitrogen with a group W where W is selected from the group CO—(C$_1$–C$_4$) alkyl; and the group (CH$_2$)$_n$COR$_o$ in which n and R$_0$ are as defined for R$_I$; and (ii) a group

(R$_{IIb}$)

in which Y is selected from a halogen atom, a (C$_1$–C$_3$) alkyl group and a (C$_1$–C$_3$) alkoxy group;

$X_1$, $X_2$ and $X_3$ are identical or different and are selected from a $(C_1-C_3)$ alkyl, a $(C_1-C_3)$ alkoxy, a halogen atom and a trifluoromethyl group;

$X_4$ is hydrogen or is identical to $X_1$, $X_2$ or $X_3$, the stereoisomers thereof and the addition salts thereof.

2. Compound of formula (I) according to claim 1, in which $R_{II}$ represents a group $R_{IIa}$ which is selected from an indole and a substituted indole and in which W, $R_I$, $X_1$, $X_2$, $X_3$ and $X_4$ are as defined for (I) and the salts thereof.

3. Compound of formula (I) according to claim 1 in which $R_{II}$ represents a group $R_{IIb}$, and in which Y, $R_I$, $X_1$, $X_2$, $X_3$ and $X_4$ are as defined for (I) and the salts thereof.

4. Compound of formula (I) according to claim 1, in which $X_1$ is in position 2, $X_2$ is in position 4, $X_3$ is in position 6 and $X_4$ is either in position 3 or 5 of the phenyl radical.

5. Compound of formula (I) according to claim 1, in which $X_1$ represents a 2-$(C_1-C_3)$ alkoxy group, $X_2$ represents a 6-$(C_1-C_3)$ alkoxy group and $X_3$, $X_4$, $R_I$ and $R_{II}$ are as defined for (I), and the salts thereof.

6. Compound of formula (I) according to claim 1, in which at least three of the substituents $X_1$, $X_2$, $X_3$ and $X_4$ are selected from $(C_1-C_2)$ alkyl and $(C_1-C_2)$ alkoxy.

7. An optically pure isomer of the compound according to claim 1.

8. Pharmaceutical composition comprising an effective amount of the compound according to claim 1, or one of the pharmaceutically acceptable salts thereof, in admixture with a pharmaceutically acceptable carrier.

9. Pharmaceutical composition according to claim 8, which is in a unit dosage form.

10. Pharmaceutical composition according to claim 8, wherein the amount of the compound is from 0.05 to 100 mg.

11. Pharmaceutical composition comprising an effective amount of the compound according to claim 7, or one of the pharmaceutically acceptable salts thereof, in admixture with a pharmaceutically acceptable carrier.

12. Pharmaceutical composition according to claim 11, which is in a unit dosage form.

13. Pharmaceutical composition according to claim 11, wherein the amount of the compound is from 0.05 to 100 mg.

14. Compound of formula (II)

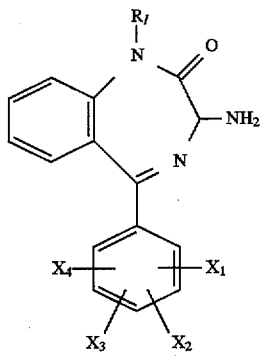

in which $R_I$ is selected from (i) hydrogen; (ii) a $(C_1-C_4)$ alkyl; (iii) a group —$CH_2$—CHOH—$(CH_2)_m$-Z in which m is selected from 0 and 1 and Z is selected from a $(C_1-C_4)$ alkyl group; $(C_3-C_8)$ cycloalkyl group; $(C_6-C_{10})$ carbocyclic aryl group optionally substituted with $(C_1-C_4)$ alkyl, $(C_1-C_4)$ alkoxy and halogen; saturated or unsaturated heterocycle selected from the group consisting of furan, thiophene, pyrrole, imidazole, pyrrolidine, piperidine, piperazine, pyridine, and morpholine, optionally substituted with a radical selected from $(C_1-C_4)$ alkyl, $(C_1-C_4)$ alkoxy and halogen; and (iv) a group —$(CH_2)_nCOR_0$ in which n is selected from 1 to 3, $R_0$ is selected from $OR_2$ and $NR_2R_3$, $R_2$ and $R_3$, which may or may not be identical, being selected from H and $(C_1-C_4)$ alkyl or alternatively $R_2$ and $R_3$ forming, together with the nitrogen atom to which they are attached, a group selected from a saturated or unsaturated heterocycle selected from the group consisting of furan, thiophene, pyrrole, imidazole, pyrrolidine, piperidine, piperazine, pyridine, and morpholine;

$X_1$, $X_2$ and $X_3$ are identical or different and are selected from a $(C_1-C_3)$ alkyl, a $(C_1-C_3)$ alkoxy, a halogen atom and a trifluoromethyl group;

$X_4$ is hydrogen or is identical to $X_1$, $X_2$ or $X_3$, the stereoisomers thereof and the addition salts thereof.

* * * * *